United States Patent
Yee et al.

(10) Patent No.: US 6,322,216 B1
(45) Date of Patent: Nov. 27, 2001

(54) TWO CAMERA OFF-AXIS EYE TRACKER FOR LASER EYE SURGERY

(75) Inventors: Kingman Yee, San Jose; Charles R. Munnerlyn, Sunnyvale, both of CA (US)

(73) Assignee: VISX, Inc, Santa Clara, CA (US)

(*) Notice: Subject to any disclaimer, the term of this patent is extended or adjusted under 35 U.S.C. 154(b) by 0 days.

(21) Appl. No.: 09/545,240

(22) Filed: Apr. 7, 2000

Related U.S. Application Data
(60) Provisional application No. 60/158,576, filed on Oct. 7, 1999.

(51) Int. Cl.[7] .................................................. A61B 3/10
(52) U.S. Cl. .................................................. 351/210; 606/5
(58) Field of Search ................................ 351/209, 210, 351/211, 212, 221, 246; 606/4, 5; 600/558

(56) References Cited

U.S. PATENT DOCUMENTS

| | | |
|---|---|---|
| 3,804,496 | 4/1974 | Crane et al. . |
| 4,169,663 | 10/1979 | Murr . |
| 4,421,486 | 12/1983 | Baldwin et al. . |
| 4,443,075 | 4/1984 | Crane et al. . |
| 4,579,430 | 4/1986 | Bille . |
| 4,669,466 | 6/1987 | L'Esperance . |
| 4,836,670 | 6/1989 | Hutchinson . |
| 4,848,340 | 7/1989 | Bille et al. . |
| 4,852,988 | 8/1989 | Velez et al. . |
| 4,950,069 | 8/1990 | Hutchinson . |
| 4,973,149 | 11/1990 | Hutchinson . |
| 5,016,643 | 5/1991 | Applegate et al. . |
| 5,098,426 | 3/1992 | Sklar et al. . |
| 5,162,641 | 11/1992 | Fountain . |
| 5,231,674 | 7/1993 | Cleveland et al. . |

(List continued on next page.)

FOREIGN PATENT DOCUMENTS

| | | |
|---|---|---|
| 42 32 021 C2 | 7/1994 | (DE) ................................. A61F/9/13 |
| 0628298 | 5/1994 | (EP) . |
| WO 94/18883 | 6/1994 | (WO) . |
| WO 95/27453 | 10/1995 | (WO) . |
| WO 99/12467 | 3/1999 | (WO) . |
| WO 99/20173 | 4/1999 | (WO) . |
| WO 99/23936 | 5/1999 | (WO) . |
| WO 99/55216 | 11/1999 | (WO) . |
| WO 00/09002 | 2/2000 | (WO) . |
| WO 00/13628 | 3/2000 | (WO) . |

OTHER PUBLICATIONS

Crane et al., "Generation–V Dual Purkinje–Image Eye-tracker," *Applied Optics* (1985) 24(4):527–537.

Machat et al., "Chiron–Technolas Keacor 116" Talamo et al., *The Excimer Manual: A Clinicians Guide to Excimer Laser Surgery* (1997) Little, Brown and Company, Inc., Chapter 12, pp. 283–298.

Rashbass et al., "New Method for Recording Eye Movement," *Journal of the Optical Society of America* (1960) 50(7):642–644.

Young & Sheena, "Survey of Eye Movement Recording Methods," *Behavior Research Methods and Instrumentation* (1975) 7(5):401–429.

*Primary Examiner*—George Manuel
(74) *Attorney, Agent, or Firm*—Townsend & Townsend & Crew LLP; Lynn M. Thompson

(57) ABSTRACT

Improved laser eye surgery and/or eye tracking systems, methods, and devices make use of two image capture devices, generally with both image capture devices disposed off the optical axis of the eye and/or any laser delivery system. This provides an enhanced imaging contrast for an imaging capture device such as a camera with a charge-couple device (CCD), particularly when using infrared imaging to track a pupil of the eye. The two off-axis cameras may be used independently to track movements of the pupil along two orthogonal lateral axes of the eye (often called X-Y tracking), and may also indicate a position of the eye along the optical or Z axis.

16 Claims, 9 Drawing Sheets

U.S. PATENT DOCUMENTS

| | | |
|---|---|---|
| 5,270,748 | 12/1993 | Katz . |
| 5,345,281 | 9/1994 | Taboada et al. . |
| 5,360,424 | 11/1994 | Klopotek . |
| 5,391,165 | 2/1995 | Fountain et al. . |
| 5,410,376 | 4/1995 | Cornsweet et al. . |
| 5,430,505 | 7/1995 | Katz . |
| 5,471,542 | 11/1995 | Ragland . |
| 5,474,548 | 12/1995 | Knopp et al. . |
| 5,556,395 | 9/1996 | Shimmick et al. . |
| 5,572,596 | 11/1996 | Wildes et al. . |
| 5,604,818 | 2/1997 | Saitou et al. . |
| 5,620,436 | 4/1997 | Lang et al. . |
| 5,632,742 | 5/1997 | Frey et al. . |
| 5,637,109 | 6/1997 | Sumiya . |
| 5,683,379 | 11/1997 | Hohla . |
| 5,752,950 | 5/1998 | Frey et al. . |
| 5,782,822 | 7/1998 | Telfair et al. . |
| 5,865,832 | 2/1999 | Knopp et al. . |
| 5,928,221 | 7/1999 | Sasnett et al. . |
| 5,966,197 * | 10/1999 | Yee ........................ 351/210 |
| 6,022,108 | 2/2000 | Yoshida et al. . |
| 6,027,216 | 2/2000 | Guyton et al. . |
| 6,027,494 | 2/2000 | Frey . |
| 6,030,376 | 2/2000 | Arishima et al. . |
| 6,159,202 | 12/2000 | Sumiya et al. ............ 606/4 |

* cited by examiner

TWO CAMERA OFF-AXIS EYE TRACKER FOR LASER EYE SURGERY

CROSS-REFERENCE TO RELATED APPLICATION

The present application is a regular patent application of and claims the benefit of priority from U.S. Provisional Patent Application Ser. No. 60/158,576 filed Oct. 7, 1999, the full disclosure of which is incorporated herein by reference.

BACKGROUND OF THE INVENTION

The present invention is generally related to measurements of the eye, and in a particular embodiment, provides methods, systems, and devices for measuring a position of an eye during laser eye surgery.

Laser-based systems are now used in opthalmological surgery on corneal tissues to correct vision defects. These systems use lasers to achieve a desired change in corneal shape, with the laser removing thin layers of corneal tissue using a technique generally described as ablative photodecomposition. Laser eye surgery techniques are useful in procedures such as photorefractive keratectomy, photothcrapeutic keratectomy, laser in situ keratomileusis (LASIK), and the like.

The ability to track or follow movements of a patient's eye is recognized as a desirable feature in laser eye surgery systems. Movements of the eye include both voluntary movements and involuntary movements. In other words, even when the patient is holding "steady" fixation on a visual target, eye movement still occurs. Tracking of the eye during laser eye surgery has been proposed to avoid uncomfortable structures which attempt to achieve total immobilization of the eye. Tracking may enhance known laser eye surgery procedures, and may also facilitate new procedures, such as treatment of irregular astigmatism.

A variety of structures and techniques have been proposed for both tracking of eye movements and scanning of a laser beam across the corneal tissue. An exemplary linear array eye-tracking system and method are described in co-pending U.S. patent Ser. No. 09/365,428 filed on Aug. 2, 1999, the full disclosure of which is incorporated herein by reference. Other systems for tracking movement of an eye, particularly for use in laser eye surgery, arc described in U.S. Pat. Nos. 5,865,832; 5,632,742; and 4,848,340, the full disclosures of which are also incorporated herein by reference.

An exemplary "offset imaging" scanning system for selective ablation and sculpting of corneal tissue is described in European Patent Application Publication No. 628298, the full disclosure of which is hereby incorporated by reference. This offset imaging system allows a relatively laser beam to be accurately directed on to a surface of a corneal tissue so as to mitigate myopia, hyperopia, astigmatism, and combinations of these ocular defects, particularly when the scanning or offset imaging system is combined with one or more variable apertures for profiling the laser beam. As described in co-pending U.S. patent Ser. No. 09/274,499, filed on Mar. 23, 1999, entitled Multiple Beam Sculpting System and Method (the disclosure of which is incorporated herein by reference), the laser beam may ideally be separated into a plurality of beamlets to minimize discontinuities adjacent the ablation edges. Alternative scanning systems are described in the following U.S. Patents, which are also incorporated herein by reference: U.S. Pat. Nos. 5,556,395; 5,683,379; 5,391,165; and 5,637,109.

Although known scanning systems have proven both effective and safe for sculpting the cornea to improve vision, work in connection with the present invention has shown that integrating eye-tracking capabilities into known laser eye surgery systems can present significant challenges. For example, known laser eye surgery systems often include an optical imaging path which is co-axial with, and shares optical elements of the laser delivery system. While it has previously been proposed to utilize imaging-based tracking systems, this shared optical path can limit the available imaging contrast, and therefore the effectiveness of the tracking arrangement.

In light of the above, it would be desirable to provide improved laser eye surgery systems, devices, and methods. It would also be desirable to provide improved eye-tracking techniques, particularly for use with laser eye surgery, with the tracker ideally providing both lateral tracking and information regarding the position of the eye along the optical axis. It would be especially beneficial if these improvements provided enhanced tracking effectiveness and allowed the incorporation of eye-tracking capabilities into known laser eye surgery systems, ideally without having to modify the laser delivery system.

SUMMARY OF THE INVENTION

The present invention generally provides improved laser eye surgery and/or eye tracking systems, methods, and devices. The invention makes use of two image capture devices, generally with both image capture devices disposed off the optical axis of the eye and/or the optical axis of any laser delivery system. This provides an enhanced imaging contrast for image capture devices such as cameras having a charge-couple device (CCD), particularly when using infrared imaging to track a pupil of the eye. The two off-axis cameras may be used independently to track movements of the pupil along two orthogonal lateral axes of the eye (often called X-Y tracking), and may also indicate a position of the eye along the optical/treatment or Z axis.

In a first aspect, the invention provides an apparatus for sculpting a corneal tissue of an eye so as to effect a desired change in a patient's vision. The apparatus comprises an energy delivery system selectively directing an energy stream toward the corneal tissue. First and second image capture devices are oriented toward the eye. A processor couples the image capture devices to the energy delivery system. The energy delivery system laterally deflects the energy stream along a first axis in response to movement of the eye sensed by the first image capture device. The energy delivery system also laterally deflects the energy stream along a second axis in response to movement of the eye sensed by the second image capture device.

The energy stream often defines a treatment axis, the eye generally being disposed within first and second fields of view of the first and second image capture devices, respectively. These fields of view are preferably angularly offset from the treatment axis, and will typically be circumferentially offset from each other about the treatment axis, often by an angle of about 90°.

Where the first image capture device is used to measure movement of the eye along an X axis of the eye, the first image capture device will preferably be disposed along an X-Z plane and angularly offset from the Y-Z plane. Similarly, where the second image capture device is used to sense movement of the eye along the Y axis of the eye, the second image capture device will often be disposed along the Y-Z plane and angularly offset from the X-Z plane. The offset angles of the first and second image capture device will typically be in a range from about 10° to 70°, the offset angle often being from about 15° to about 65°, preferably being from about 20° to about 50°, and more preferably being from about 25° to about 45°. The exemplary embodiment has offset angles of about 27°.

In another aspect, the invention provides an apparatus for sensing motion of an eye. The eye has an optical axis and first and second lateral optical axes. The apparatus comprises a first tracker with a first image capture device and a first processor module. The first image capture device is oriented towards the eye along a first imaging axis. The first imaging axis is angularly offset from the optical axis. The first processor module generates a first signal indicating lateral movement of the eye relative to the first imaging axis. A second tracker with a second image capture device and a second processor module is also provided. The second image capture device is oriented toward the eye along a second imaging axis. The second imaging axis is angularly offset from the optical axis and displaced circumferentially from the first imaging axis relative to the optical axis. The second processor module generates a second signal indicating lateral movement of the eye relative to the second imaging axis.

A third processor module can be coupled to the first and second trackers. The third processor module calculates lateral displacement of the eye along the first and second lateral axes from the first and second signals, which allows calculation of movement along the optical axis.

In a method aspect, the invention provides a method for sensing movement of an eye having an optical axis and first and second lateral axes. The method comprises sensing movement of the eye along the first lateral axis with a first image capture device. The first capture device is disposed along a first imaging path offset from the optical axis. Movement of the eye along the second lateral axis is sensed with a second image capture device disposed along a second imaging path offset from the optical axis. The second imaging path is displaced circumferentially from the first imaging path relative to the optical axis.

Preferably, a pattern of laser energy is directed toward the eye so as to effect a desired change in an optical characteristic of the eye. The laser energy may be displaced laterally in response to the sensed movement of the eye from the first and second image capture devices to enhance alignment between the pattern and the eye when the eye moves. Position and/or movement of the eye along the optical axis may be calculated using information from the first and second image capture devices. In some embodiments, the eye movement sensing system and/or laser beam deflection system may not move rapidly enough to follow the fastest involuntary or saccadic movements of the eye, but will effectively track movements of the eye which are at speeds associated with involuntary eye movements during visual fixation. Other embodiments may provide performance sufficient to track most and/or all eye movements (including saccadic eye movements), with these high-performance systems often including image capture devices with high sampling rates.

DESCRIPTION OF THE SPECIFIC EMBODIMENTS

The present invention generally provides improved methods for sensing movement of an eye, particularly for use in laser eye surgery. The systems of the present invention will often include two off-axis image capture devices, with each image capture device sensing movement of the eye along an associated lateral eye movement axis. The image capture devices, sometimes referred to herein as cameras, will typically be disposed off of the optical axis of the eye, which is often (but not necessarily) co-axial with the treatment axis of the laser system. The lateral movements of the eye tracked by the two off-axis camera system will often be described with reference to horizontal and vertical motions. As used herein, horizontal motions are from right to left or left to right relative to the patient, while vertical motions are along the inferior/superior orientation relative to the patient. It should be noted that the first and second motion axes associated with the first and second image capture devices need not necessarily be orthogonal, and that even when these motions axes are orthogonal (such as when they define orthogonal X and Y lateral orientations) they need not necessarily be aligned with the horizontal and vertical orientations.

Figure 1:
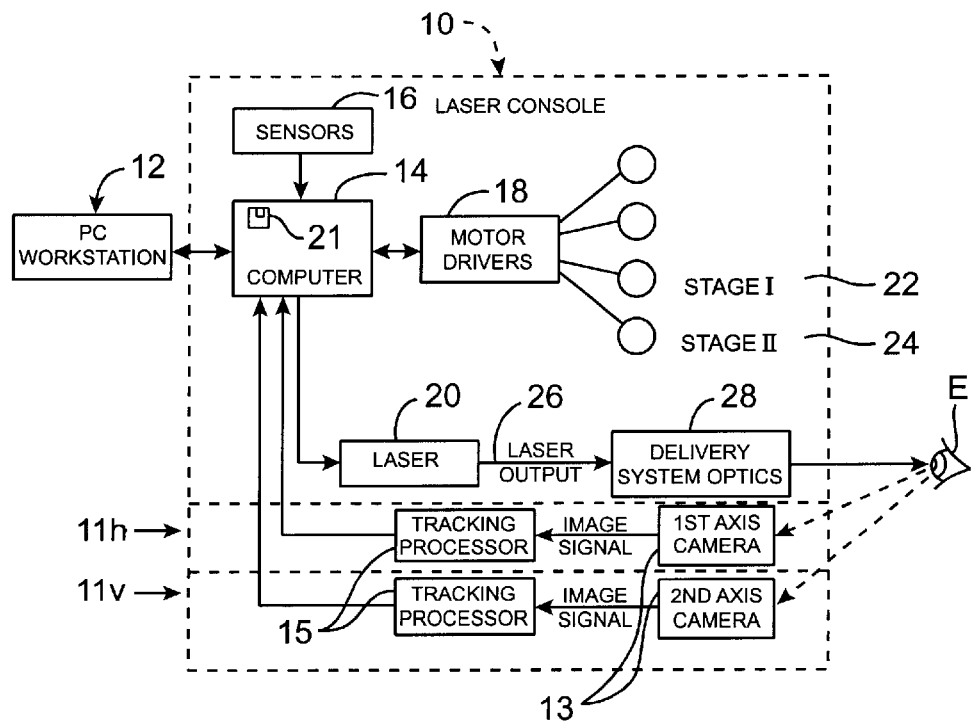
FIG. 1 is a simplified block diagram of an opthalmological surgery system incorporating the invention.

Referring now to FIG. 1, an opthalmological surgery system 10 has horizontal and vertical trackers 11h, 11v. Each of trackers 11 include a camera 13 and an associated tracking processor 15. Where differentiated in the following description, these components may be referred to as horizontal camera 13h, vertical camera 13v, and the like.

Opthalmological surgery system 10 typically also includes a laser 20 which generates a laser beam 26 that is selectively directed toward eye E by delivery system optics 28. Delivery system optics 28 scan beam 26 over the corneal tissue of eye E according to instructions from computer 14. The computer generally scans beam 26 over eye E by changing the angular position of first and second stage pivot systems 22, 24 (described below). In alternative embodiments, the computer may scan the beam by pivoting one or more mirrors using galvanometric motors, or any of a wide variety of alternative scanning mechanisms. Optionally, computer 14 may direct profiling of beam 26 using one or more variable apertures.

As also shown in FIG. 1, system 10 includes a personal computer workstation 12 coupled to computer 14. Laser surgery system 10 may include a plurality of sensors (generally designated by reference no. 16) which produce feedback signals from moveable mechanical and optical components, such as those described in European Patent Application Publication No. 628298, previously incorporated herein by reference. PC workstation 12 and computer 14 may be combined in a single processor structure, or these processing functions may be distributed in a wide variety of alternative arrangements. Similarly, tracking processor modules 15 may comprise one or more separate processing structures from computer 14, or may be integrated into computer 14 as a single processor or with a wide variety of distributed processing arrangements. Computer 14 may comprise a tangible medium 21 embodying the methods of the present invention in a machine readable code. Suitable media include floppy disks, compact optical disks (CDs), removable hard disks, or the like. In other embodiments, the code may be downloaded from a communication modality such as the Internet, stored as hardware, firmware, or software, or the like.

In response to signals provided by tracking processor modules 15 and sensors 16, and according to the scultping to be performed on the eye to alleviate an optical defect, computer 14 transmits command signals to motor drivers 18 and to laser 20. In response to these command signals, motor drivers produce signals to change an angular orientation of first stage pivot system 22 and second stage pivot system 24, and to operate the other components of the laser delivery system, such as to vary a size of a variable diameter iris to correct myopia, to control the distance between a pair of parallel blades so as to vary a width of the laser beam, to rotate an angular orientation of the parallel blades and rectangular beam to correct astigmatism, and the like. Computer 14 can compensate for lateral movement of the eye during a sculpting procedure by directing the motor driver to reposition the beam (typically by movement of the first and second stages 22, 24) so that the therapeutic pattern of laser energy which is to be directed at the eye remains aligned with the eye during voluntary and/or involuntary movements of the eye.

In broad terms, the horizontal and vertical cameras 13 capture images of the eye from along imaging paths which are offset from the treatment axis of beam 26. The cameras, which typically comprise infrared sensitive charge couple devices (CCD) generate image signals which are transmitted to the tracking processor modules 15. The tracking processor modules calculate a position of a feature of the eye, and transmit signals indicating the position to computer 14. These signals may comprise an absolute position of the feature relative to the laser system, a relative position of the feature, a size of the feature, and the like. In some embodiments, the positional information may comprise a velocity of the feature, an acceleration of the feature, or the like. If sufficient tracking system performance is desired to track the more rapid involuntary saccadic movements of the eye, cameras 13 may comprise high-sampling rate image capture devices, often with a sampling rate of about 250 Hz or more.

Figure 2:
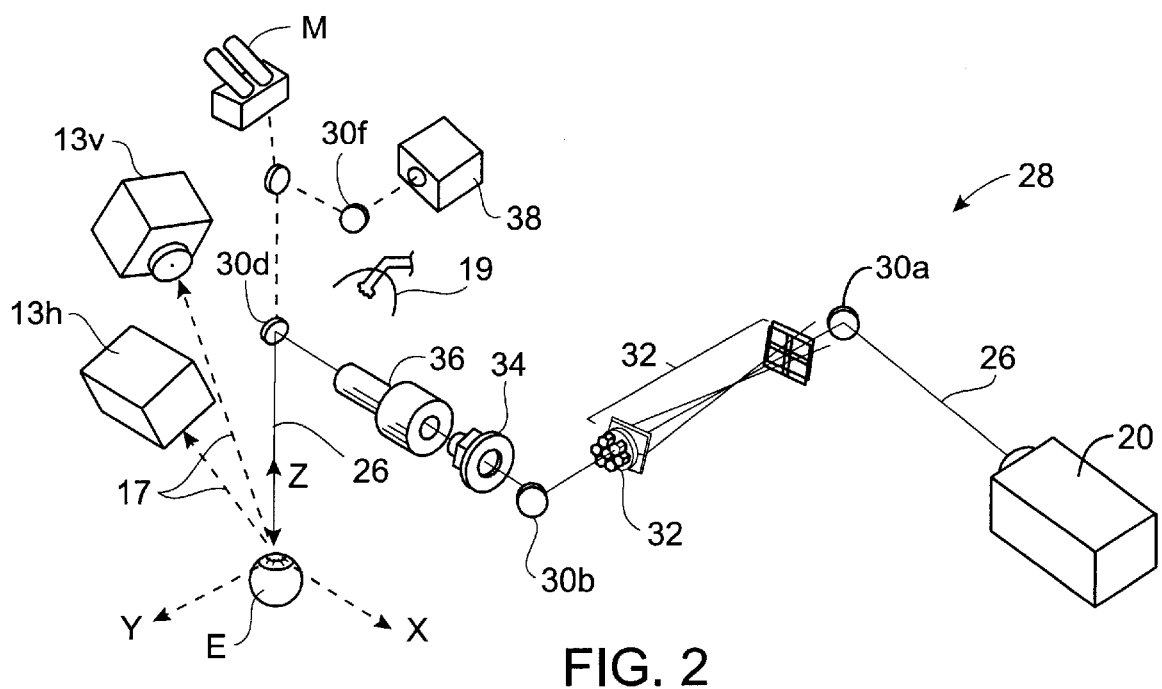
FIG. 2 is a simplified perspective view of the laser delivery optics and tracking imaging axes of the system of FIG. 1.

Typical delivery system optics 28 are illustrated without their associated support structure in FIG. 2. Mirrors 30a and 30b (mirrors 30a, 30b . . . generally being referred to as mirrors 30) direct laser beam 26 through spatial and temporal integrators 32 and a variable aperture 34 prior to entering a scanning mechanism 36. Scanning mechanism 36 (which includes the first and second stages) selectively deflects beam 26 laterally across the corneal surface of eye E in the X-Y plane. While a laser system having a relatively large beam cross-section is shown, the tracking system will also provide advantages for a wide variety of laser eye surgery systems, including those having small-spot scanning lasers.

A variety of lenses may be provided for imaging, viewing the procedure using microscope M, and the like. Tracking systems 11 monitors movement of eye E, so that computer 14 can compensate for the eye movement and accurately ablate the intended portion of the treatment area. A particularly advantageous eye tracker camera/processor is commercially available from ISCAN, INC. of Burlington, Mass. Ideally, tracking systems 11 are suitable for integration into VISX START™ and VISX STAR S2™ laser eye surgery systems, which are commercially available from VISX, INCORPORATED of Santa Clara, Calif. Alternatively, embodiments of the present tracking system may be incorporated into laser systems commercially available from CHIRON VISION of Irvine, Calif. (a division of BAUSCH & LOMB); NIDEK CO., LTD. of Gamagori, Japan; LASER SIGHT, INC. of Orlando, Fla.; AUTONOMOUS TECHNOLOGIES CORPORATION of Orlando, Fla.; and a variety of others.

Laser 20 may include, but is not limited to, an excimer laser such as an argon-fluoride excimer laser producing laser energy with a wavelength of about 193 nm. Alternative laser systems may include solid state lasers, such as frequency multiplied solid state lasers, flash-lamp and diode pumped solid state lasers, and the like. Exemplary solid state lasers include UV solid state lasers producing wavelengths of approximately 188–240 nm such as those disclosed in U.S. Pat. Nos. 5,144,630, and 5,742,626; and in Borsuztky et al., Tunable UV Radiation at Short Wavelengths (188–240 nm) Generated by Frequency Mixing in Lithium Borate, *Appl. Phys.* 61:529–532 (1995). A variety of alternative lasers might also be used. The laser energy will generally comprise a beam formed as a series of discreet laser pulses, and the pulses may be separated into a plurality of beamlets.

FIG. 2 also illustrates the position and orientation of horizontal and vertical cameras 13h, 13v. Horizontal camera 13h primarily measures movement of eye E along the X axis of the eye, and is positioned along the Y-Z plane and offset from the X-Z plane. Vertical camera 13v primarily measures movement of eye E along the Y axis, and is disposed along the X-Z plane and offset from the Y-Z plane, as illustrated. The horizontal and vertical cameras 13h, 13v are oriented toward eye E along optical image paths 17 centered within fields of view of the cameras, with these optical paths generally defined by lenses of the associated camera structures.

The horizontal and vertical cameras, together with the tracking processor modules, will often comprise commercially available tracking systems such as those available from ISCAN, INC. of Burlington, Mass., or other comparable systems. Suitable tracking systems will generally include a position sensor and a processor for generating a position signal in response to signals from the sensor. Preferred tracking systems will typically include a two dimensional optical position sensor, often with optics for imaging the eye onto the sensor. The exemplary system includes both an infrared CCD camera and a personal computer interface (PCI) card, together with software drivers compatible with an operating system running on computer 14, such as Windows NT ™ from MICROSOFT®. Cameras 13 may include a 1.25" square by 0.3" thick printed circuit board powered by a 12 volt power source. Alternative camera structures having larger and/or smaller dimensions may be powered by a variety of sources, and may sense light in the visible or other wavelength ranges. As described above, the camera provides an image signal to an associated tracking processor 15, which will typically be in the form of a tracking card.

In use, eye E will be illuminated with an infrared illumination source illustrated schematically at reference numeral 19. Infrared source 19 will preferably comprise one or more infrared light-emitting diodes (LEDs). In the exemplary embodiment, lighting is provided by two banks of three infrared LEDs each, with each LED consuming about 80 ma of electrical current. These banks of light-emitting diodes may be selectively energizable, with one bank of LEDs being energized only when the right eye is aligned with a treatment axis of the laser system, and the other bank being energized only when the left eye is aligned with the treatment axis. The LEDs will typically be within 90° (longitude) from the cameras, and will preferably have a larger azimuth angle (latitude from veritical) than cameras 13.

Under the infrared illumination provided by infrared source 19, the pupil of eye E will appear relatively dark to cameras 13, as the infrared energy is not directly reflected by this clear structure. The area surrounding the pupil, including both the iris and sclera, will present a much lighter shade to cameras 13 under the infrared illumination, thereby producing a high contrast image of the pupil for tracking.

Because ambient lighting of eye E may change during a procedure, the size of the tracked pupil may also change. To accommodate the changing size of the pupil, dynamic thresholding is a highly advantageous feature of the exemplary commercially available tracking camera. Dynamic thresholding is achieved by determining the pupil size while adjusting the threshold.

As described above, scanning mechanism 36 will preferably laterally deflect beam 26 in response to movement of eye E sensed by cameras 13. The scanning mechanism is seen most clearly in FIG. 3. The scanning mechanism 36 generally laterally deflects laser beam 26 by pivoting an imaging lens 40 about a first axis 42, and about a second axis 44. More specifically, scanning mechanism 36 includes a fixed support structure in the form of bracket 46. A first stage 48 pivots about first axis 42 relative to bracket 46, while a second stage 50 pivots relative to first stage 48 about second axis 44.

Figure 3:
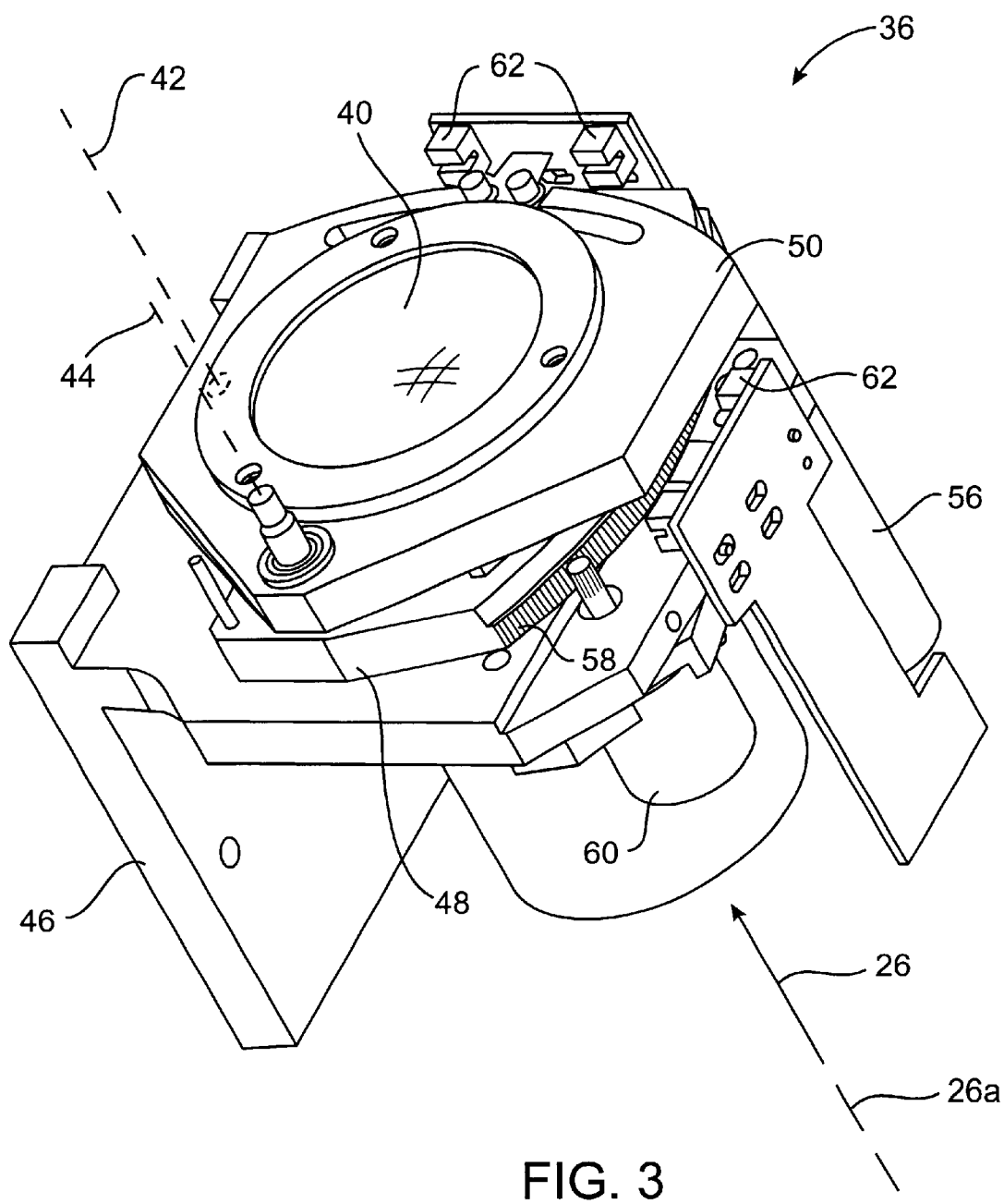
FIG. 3 is a perspective view of an exemplary scanning mechanism for use in the laser delivery system of FIG. 2.
Figure 3A:
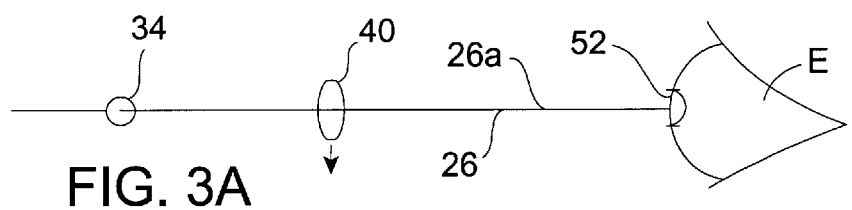
FIGS. 3A, 3B, and 4 illustrate the operation of the scanning mechanism of FIG. 3.
Figure 3B:
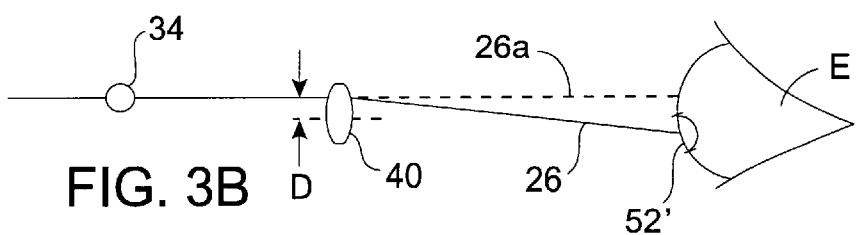

The deflection of beam 26 from an undeflected beam axis 26*a* can be understood with reference to 3A and 3B. By pivoting the first and second stages about pivotal axes extending along and outside of beam 26, imaging lens 40 is displaced by a variable distance D from initial beam axis 26*a*. Displacing imaging lens 40 from initial axis 26*a* displaces an image 52 of variable aperture 34 from initial axis 26*a* to an offset aperture image 52'. The amount and direction of movement of the aperture image is related (but not necessarily proportional) to the amount and direction of lens offset D. Hence, to reposition aperture image 52 across the corneal surface, the offset structure moving lens 40 will preferably allow the lens to be moved directly both above and below initial axis 26 as illustrated in FIG. 3, and also into and out of the plane of the drawing, thereby allowing scanning of the ablative laser energy in the X-Y plane across the corneal tissue. Alternative laser delivery systems may scan a beam having a constant profile, or the beam profile and intensity might be varied by a variable magnification system. The present invention therefore encompasses systems without variable apertures.

Figure 4:
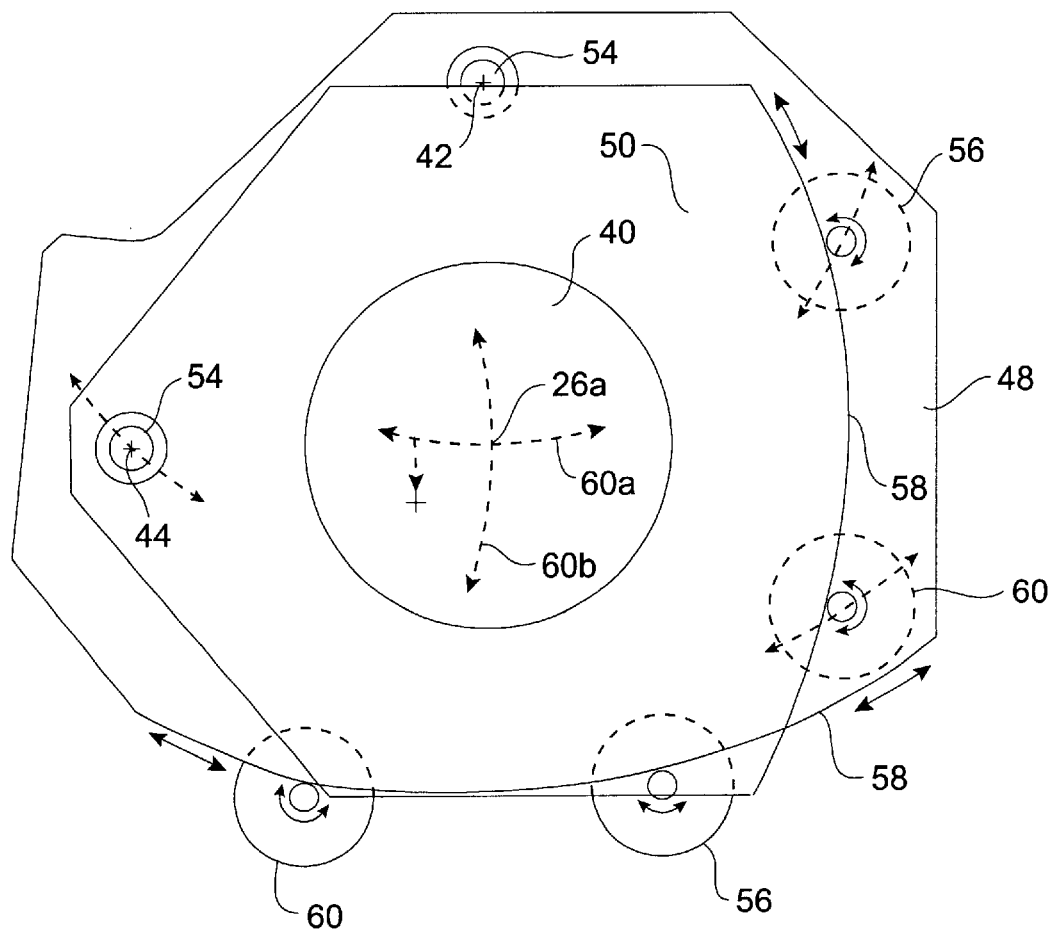

The X-Y scanning capabilities of scanning mechanism 36 can further be understood with reference to FIGS. 3 and 4. First stage 48 is pivotally mounted to bracket 46 by a pivotal joint 54. Pivotal joint 54 defines first pivotal axis or pivot 42, and the first stage rotates about the first pivot due to driving engagement between a motor 56 and a drive surface 58 of the first stage. An encoder 60 also engages drive surface 58, so as to provide feedback to the computer 14 regarding the angular orientation of the first stage. Second stage 50 is mounted to first stage 48 by another pivotal joint 54 defining second pivotal axis or pivot 44. Imaging lens 40 is mounted to second stage 50, so that the imaging lens moves with the first stage when the first stage pivots about pivot 42 along arc 60*a*.

To angularly reposition the imaging lens about the second axis, a motor 56 is mounted to first stage 48 and drivingly engages a drive surface 58 of second stage 50. Feedback to computer 14 is again provided by an encoder 60, which is also mounted to first stage 48.

The pivotal motion of first stage 48 relative to bracket 46 allows imaging lens 40 to be displaced about pivot 42 along a first arc-shaped path 60*a* on either side of initial beam access 26*a*. To provide X-Y scanning of laser beam 26 to an arbitrary location within a treatment zone on a corneal surface of the eye, motor 56 mounted to first stage 48 pivots second stage 50 about pivot 44, thereby moving offset lens 40 along a second arc-shaped path 60*b* which intersects the first arc-shaped path. In the exemplary embodiment, pivots 42 and 44 are offset about the initial beam axis 26*a* by about 90°, so that the first and second arc-shaped paths 60*a*, 60*b* also intersect by about 90°.

Accurate positioning of the laser energy on the X-Y plane adjacent the corneal surface should accommodate the arc-shaped motion of the image by adjusting the angular position of the lens about the first and second pivots 42, 44. In other words, the pivots approximate motions in the X and Y directions, and the system 10 compensates for the resulting nonlinearity of the beam deflection by additional movement of the complementary stage, as can be understood with reference to FIG. 4. A wide variety of algorithms might be used to compensate for the arc-shaped beam deflection of the dual pivot imaging lens support of the present invention. Computer 14 may simply model the substantially arc-like movement of the laser beam based on the kinematic structure of scanning mechanism 36 and the optical properties of lens 40. Alternatively, a look-up table may be created of the desired angular positions of the first and second stages for discreet X and Y target coordinates, with standard interpolation routines used between the discreet table entries.

Computer 14 of the system illustrated in FIG. 1 calculates the desired angular position of the first and second stages based in part on the location of the pupil sensed by horizontal and vertical cameras 13*h*, 13*v*. Preferably, computer 14 will determine a position of the pupil relative to the optical axis of the eye and/or of the laser delivery system using calculations which can be understood with reference to FIG. 5. These calculations are shown for the horizontal camera 13*h*, which is illustrated here schematically by an imaging lens of the camera. It should be understood that the vertical camera may make use of similar calculations, except that the vertical camera 13*v* will instead be located at a position 90° offset from the horizontal camera about Z, the optical axis of the eye E and/or treatment axis of the laser beam 26. As the horizontal camera 13h has 380 horizontal pixels and 350 vertical pixels, the horizontal axis of the camera $X_H$ is aligned along the X axis. To minimize distortion along this desired measurement axis while providing an enhanced contrast, horizontal camera 13h is disposed along the X-Z plane and is offset from the Y-Z plane by an angle ξ. ξ may be in a range from about 10° to about 70°, often being between about 15° and 65°, preferably being between about 20° and 50°, and ideally being between about 25° and 45°, ξ being about 27° in the exemplary embodiment.

Figure 5:
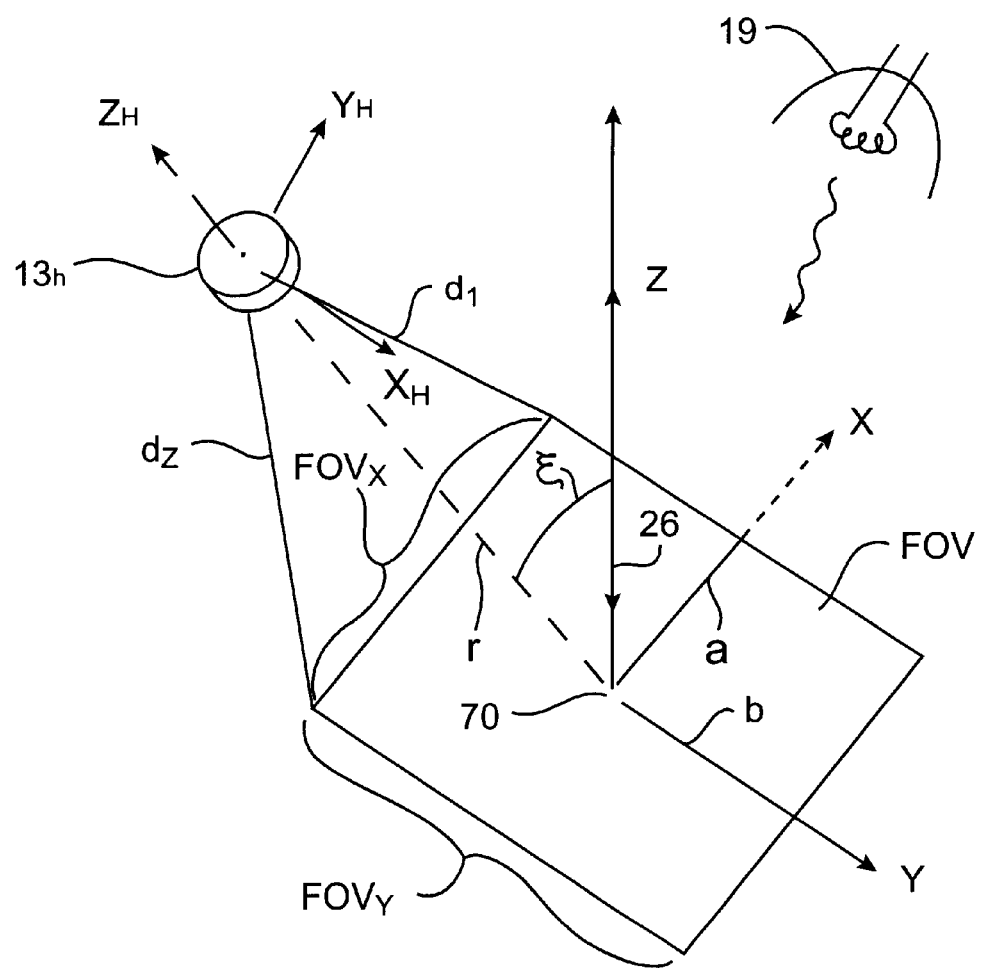
FIG. 5 schematically illustrates a position of a camera for sensing movement of the eye along a first or X axis of the eye, and graphically illustrates coordinate systems of the camera and eye, together with variables used in transforming movement sensed by the camera to measurements of lateral eye movements.

First introducing some of the variables used in the following calculations as illustrated in FIG. 5, horizontal camera 13h images a region or field of view (FOV) of eye E which is substantially rectangular in shape, with a width indicated by $FOV_y$ and a height indicated by $FOV_x$. The eye surface region imaged within this field of view will generally be at an angle of ξ relative to the camera. The center 70 of the field of view is separated from camera 13h by a distance r, the top edge of the field of view is separated from the treatment center 70 by a distance a, and the side edge of the field of view is separated from the treatment center 70 by a distance b. The corners of the field of view FOV are separated from camera 13h by distances $d_i$, with i being 1, 2, . . . As the field of view is generally symmetric about the Y-Z plane, the two distances of interest are $d_1$ and $d_2$, as illustrated.

Where x is the coordinate of the pupil along the X-axis of the coordinate system of the eye, and y is the coordinate of the pupil center along the Y-axis of the eye's coordinate system, we will first determine the correct scaling factor $Scale_x$ for the Y-component in the horizontal camera and the X-component in the vertical. The scale factor is used to calculate the y value. From the horizontal camera, using the equation:

$$y=(1-Scale_x x)y_H$$

in which x is equal to the x component provided by the vertical camera, and $y_H$ is equal to the y component provided by the horizontal camera. To determine the scaling factor, we first calculate the distances to the corners of the field of view (FOV) $d_1 d_2$ from:

$$d_i=\sqrt{b^2+a^2+r^2-2ar\cos(\theta_i)}$$

in which $\theta_1$ is equal to π/2+ξ and $\theta_2$ is equal to π/2–ξ. The scale factor can then be calculated by the ratio of the angle subtended by lines $d_1 d_2$ at a given FOV in either millimeters or pixels from:

$$Scale_x[pixels] = \left(1 - \frac{\sin^{-1}\left(\frac{FOV_y}{2d_1}\right)}{\sin^{-1}\left(\frac{FOV_y}{2d_2}\right)}\right)/N_x$$

$$Scale_x[mm] = \left(1 - \frac{\sin^{-1}\left(\frac{FOV_y}{2d_1}\right)}{\sin^{-1}\left(\frac{FOV_y}{2d_2}\right)}\right)/FOV_x$$

in which $N_x$ is the number of pixels spanning the field of view (FOV) in the x direction $FOV_x$. $y_H$ may have units of either millimeters or pixels, depending on the coordinate system used, and will provide a value for y having similar units. These calculations are an example of one method for calculating scaling factors. In other embodiments, scaling factors may be measured rather than calculated.

As described above, calculation of x follows a similar analysis, in which the scaling factor (here in millimeters) is:

$$Scale_x[mm] = 1 - \frac{\sin^{-1}\left(\frac{FOV_y}{2d_1}\right)}{\sin^{-1}\left(\frac{FOV_y}{2d_2}\right)}/FOV_x$$

and in which x is calculated using this scaling factor from the following equation:

$$x=(1+Scale_y y)x_v$$

As both the horizontal and vertical cameras provide two-dimensional information at an angle to the treatment axis Z, the position of eye E along the treatment axis Z may also be calculated. More specifically, the position of the pupil measured by the horizontal camera $x_H$ in the coordinate system of the horizontal camera has a z-component as follows:

$$x_H=x+z\tan(\xi)$$

Similarly, measurement provided by the vertical camera $13_v$ have a z-component as follows:

$$y_v=y-z\tan(\xi)$$

(as the exemplary vertical camera $13_v$ images the eye from an inferior position). Solving for z (the position of the eye along the Z axis), with x known from the vertical camera and y known from the horizontal camera, we find that:

$$z = \frac{x_H + x}{\tan(\xi)}$$

$$z = \frac{y_V - y}{\tan(\xi)}$$

Figure 7:
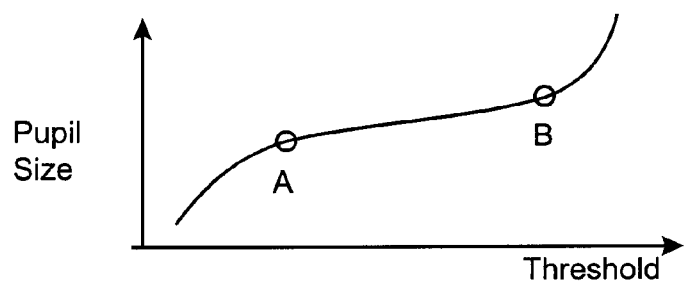
FIG. 7 graphically illustrates pupil brightness threshold optimization as used in the system of FIG. 2.

As schematically illustrated in FIG. 7, tracking of eye E will preferably be relative. In other words, when the system operator initiates tracking, the tracking system records a position of pupil P as an initial position $P_O$ having a reference center location O. Subsequent eye movement is tracked relative to this central reference position O. Hence, absolute alignment of the tracker is not critical. However, tracking benefits significantly from accurate rotational alignment of the tracker components, as rotational misalignment may be more difficult and/or impossible to compensate for using software and the like.

A movement vector of the eye E relative to the initial reference may be calculated as a vector $\dot{E}$ according to the equations given above as:

$$\dot{E}=x\hat{i}+y\hat{j}+z\hat{k}$$

Figure 6:
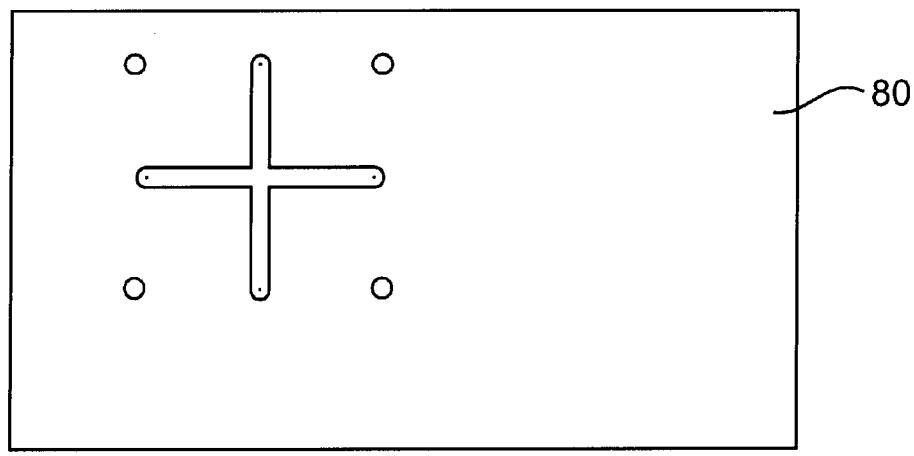
FIGS. 6 and 6A illustrate a camera calibration tool for use with the system of FIG. 1.
Figure 6A:
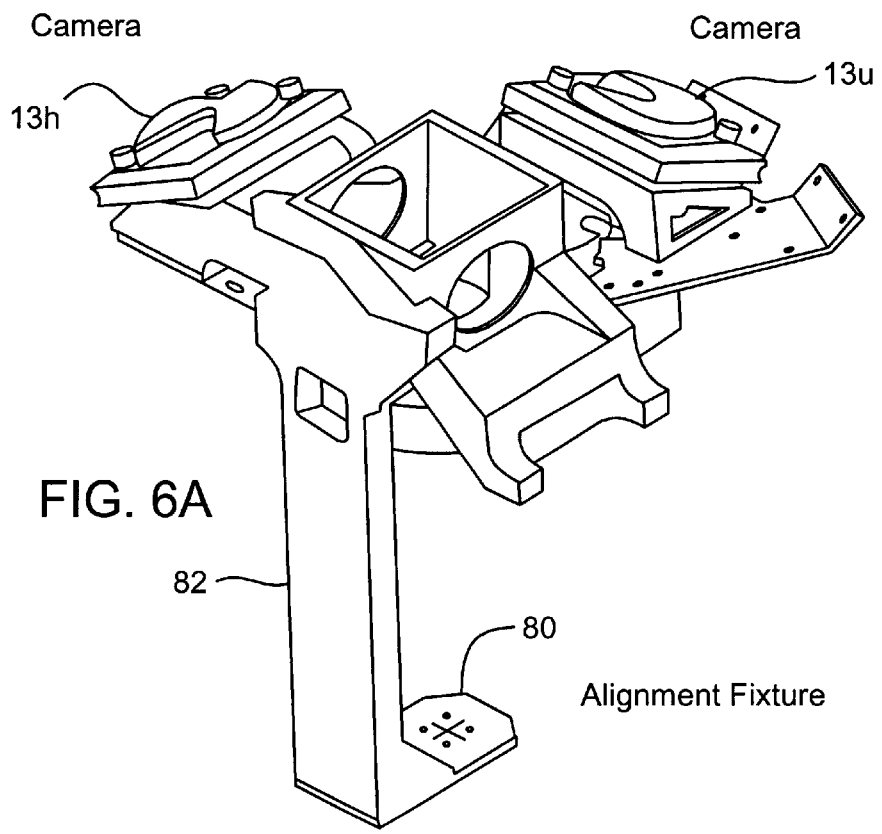

Referring now to FIGS. 6 and 6A, a calibration jig 80 may be removably supported at the treatment position for eye E to align the horizontal and vertical cameras 13h, $13_v$, so as to zero the x and y values provided by the camera, and so as to orient the cameras properly about their optical axes. A fixture 82 holds the pattern of jig 80 at the desired position during calibration. To provide adjustability, the cameras are mounted so as to have three axes of rotation. Adjustments about these axes will preferably be provided by fine screw adjustment mechanisms with lock-downs provided to secure the position of the camera once calibration jig 80 appear; at the desired position and orientation. The range of motion of cameras 13 about the camera mount axes of rotation are typically a total of about 5° or more.

The structure and arrangement of the exemplary horizontal and vertical cameras 13h, 13v can also be seen clearly in FIG. 6A. The cameras are offset lateral left and an inferior position relative to the optical axis of the patient by about 27°. The exemplary eye tracker system includes two dedicated eye tracker cards coupled to two small infrared cameras. A plurality or bank of infrared light emitting diodes provide oblique elimination, the exemplary light omitting diodes producing light having a wavelength of about 880 nm. This arrangement allows the video-based system to detect the darkness of the pupil, as the pupil acts as a light sink while the surrounding iris has a relatively light shade. The camera includes a 1.25"×1.25"×3.0" printed circuit board powered by the a 12v source. The contrast threshold can be actively set, with dynamic thresholding often being initiated prior to treatment. The exemplary eye tracking system uses a 60 hz system producing a sample or eye location signal along an associated axis every 16.7 ns.

The exemplary alignment fixture 82 and jig 80 position the alignment pattern below the treatment plane, the alignment pattern ideally being more than 1.0 mm below the treatment plane, with the exemplary alignment pattern being about 3.5 mm below the treatment plane. This offset will compensate for an average distance between a corneal surface and the patient's iris. Jig 80 generally comprises a plate with a pattern, the ideal pattern including four holes disposed at the four corners of a square (ideally of a square having sides of 14 mm) and a cross at the center of the square. This facilitates determination of the optical center and rotational alignment of the cameras. The holes are also useful for calibration of camera resolution and calculation of scale factors in micrometers per pixel. This exemplary pattern is illustrated in FIGS. 6 and 6A. Rotational alignment of the cameras may be facilitated by generating a crosshair on the eye tracker display and rotating each camera to align the crosshair with the pattern. A scale factor of about 56.7 $\mu$m per pixel may be used.

The images provided by the two cameras are processed by their associated PCI cards to determine a centroid of the pupil in the horizontal and vertical orientations. The pupil centroid data is available to the processor and/or processors of the laser treatment system when the tracker software triggers an interrupt. A datastream from the cameras may contain duplicates as both horizontal and vertical data may be generated from each camera whenever either camera triggers a new image interrupt. A C++ program may be used to remove duplicate data and maintain alignment to the data from the two cameras. Optionally, this duplicate data may be used to verify that both trackers are operating within a predetermined tolerance, and/or to determine a vertical position of the pupil, as described above. If the trackers appear to out of tolerance or if the patient's eye moves horizontally and/or vertically beyond a safe tracking/treatment zone, treatment may be interrupted. Timing information and the most recent pupil position are generally available to system programming via a data request/interrupt at all times.

An exemplary method and system for generating a tracking threshold can be understood with reference to FIG. 7. In general, both a threshold level or value and gated area are determined to facilitate tracking of the pupil. The gated area will generally comprise a limited region of interest (ROI) within the image, the exemplary gated area comprising a rectangle within the image. Pixels inside the gated area are candidates for inclusion in the pupil, while pixels outside the gated area are excluded from potential inclusion within the pupil. Preferably, the gated area is selected so as to be as large as possible, while excluding unwanted edge material or features, such as a Lasik flap, eyelid, flap protector, speculum, or the like. The use of such a gated area helps to eliminate undesired artifacts near the edges of the field of view, but might also cause distortion as the pupil crosses the gated area boundary. Preferably, each tracking system will apply a variety of tests before accepting a pupil position as valid, including a minimum separation between a pupil centroid and a gated area boundary, and the like. If any of these tests are not fulfilled, a tracking error condition may be identified, and a tracking error signal may be generated.

Each time a system operator initiates a treatment with the laser eye surgery system 2, the application may "dynamically threshold" or generate a pupil threshold level automatically. In the exemplary embodiment, this can be accomplished by acquiring a number of separate images at differing illumination threshold settings. Pupil size may be calculated for each of these differing images, and the pupil sizes may be analyzed as a function of threshold setting, as illustrated in FIG. 7. The threshold/pupil size curve has a characteristic shape in which the curves gradient is generally below a predetermined or assigned value between points A and B. The gradient generally increases beyond these two points along the curve, so that the optimum threshold value is somewhere between A and B on the relatively flat part of the curve. The exemplary threshold level setting is determined from the equation:

Optimum Position is equal to $A+(B-A)$Threshold Ratio:

in which threshold ratio is an assigned value typically being between zero and one.

Figure 8:
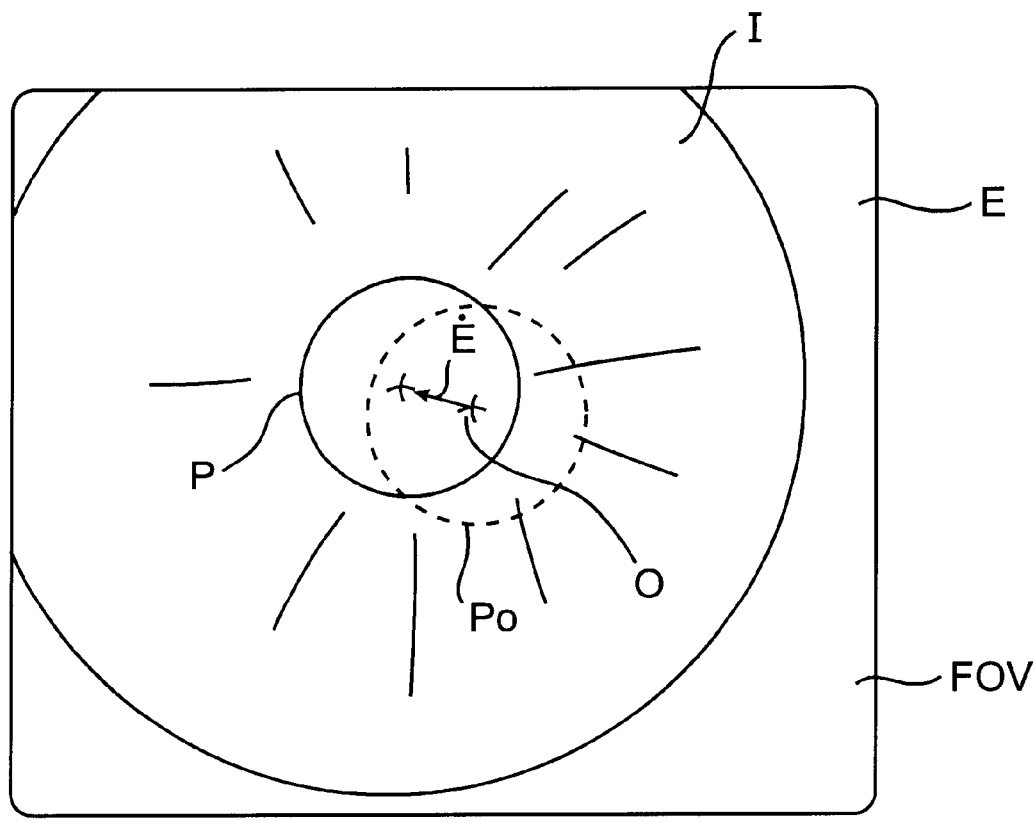
FIG. 8 schematically illustrates an image captured by the image capture devices of the system of FIG. 1, and shows a method for using that image to provide relative positioning information.

Referring to FIGS. 2 and 8, a typical laser surgery procedure will proceed with the system operator positioning the patient while the tracker is off. The system operator will then position the laser delivery optics relative to the patient's eye E with the horizontal and vertical cameras 13 mounted relative to the delivery system optics so that they are also aligned with eye E. A microscope M is focused on eye E and the tracking system is enabled by the system operator inputting a command to the system, typically by pressing a keypad button.

The system operator aligns eye E with a reticle of microscope M, so as to establish the reference position of the tracker. Once the eye is aligned, the system operator provides another input command, such as by pressing a foot switch. The pupil position at the time of this second input command O is the tracker origin.

The tracker thereafter gives movement coordinate vectors to the system from the tracker origin. In many embodiments, an indication will be displayed to the operator, optionally as a light within the field of view of microscope M to show that tracking is operative. The eye tracker will generally remain on until another input command from the system operator, such as again pressing the keypad button, with the button toggling the tracker on and off.

If tracking is lost during a treatment (for example, while the system operator intends to maintain a treatment by continuing to depress a foot peddle), a loss of tracking indication may be provided to the system operator, such as by providing a flashing indicator within the microscope or on any other system display. Optionally, laser sculpting may be automatically interrupted if tracking is lost. If the procedure is interrupted prior to completion (in many laser eye surgery system, by partially releasing a foot peddle) the tracker may keep the stored reference position until and/or unless the procedure is fully interrupted by releasing the foot peddle fully, or the like.

Experimental

Eye motion and tracking data were recorded in a clinical setting to determine whether the eye tracking system of FIGS. 1, 2, and 6A can track eye motions. Four ophthalmologists were recruited to participate in the study. A recording system was implemented such that the doctors were allowed to perform surgical procedures on 45 eyes as they normally would, while generating positional information with the above-described two-camera system, but without redirecting the ablative laser pattern in response to the positional information. The surgical procedure was performed using a VISX STAR S2™ excimer laser system on which the horizontal and vertical offset camera tracking system was mounted.

To evaluate accuracy of tracking in a clinical setting, a validation tracking system was compared with the positional data generated from the two-camera off-axis tracker. The validation tracking system was not a real-time system, and functioned as a digital video tape recorder during laser eye treatment. The validation tracker recorded eye images every 5 ms, with eye position being determined retrospectively in the lab and compared to the real-time data obtained during recording using the two-camera off-axis tracker.

The two-camera eye tracker system and the validation tracker 38 were connected to a computer independent of the excimer laser system computer for these tracking tests, and synchronization of the two-camera tracker and the validation tracker were accomplished to within 0.1 ms by hardware triggers. Pressing the start/acquire button started the trackers substantially immediately, although the asynchronous cameras produced tracker data with a latency of zero to 16.7 ms (up to one frame), while the 200 Hz validation tracker began acquisition within 0.1 ms and produced an image 5 ms later. The two-camera off-axis tracker cameras and LED power were externally connected to provide 5 volts to the LEDs, and 12 volts to the cameras. The camera outputs were grounded to the excimer laser system, and connected directly to the eye tracker cards. The eye tracker cards generated a video output containing the camera video with an overlay showing the pupil's center.

The eye tracker video outputs were connected to a distribution amplifier and connected into a pair of analog video acquisition cards and to a pair of video cassette recorders. The video was recorded in both digital and analog formats.

Illumination for the validation camera 38 was visible light. The majority of illumination was provided by oblique lights of the excimer laser system. Because different doctors operate at different levels of illumination, the image brightness and contrast were not constant, and the doctor was free to use a desired illumination amount during treatment.

Tracking data from the two-camera tracker and the validation tracker were taken from 29 patients, with recording being made during treatment of a total of 45 eyes, including 19 left eyes and 26 right eyes. The average correction during the laser procedure was −4.84D of sphere with −0.63D of cylinder.

Figure 9:
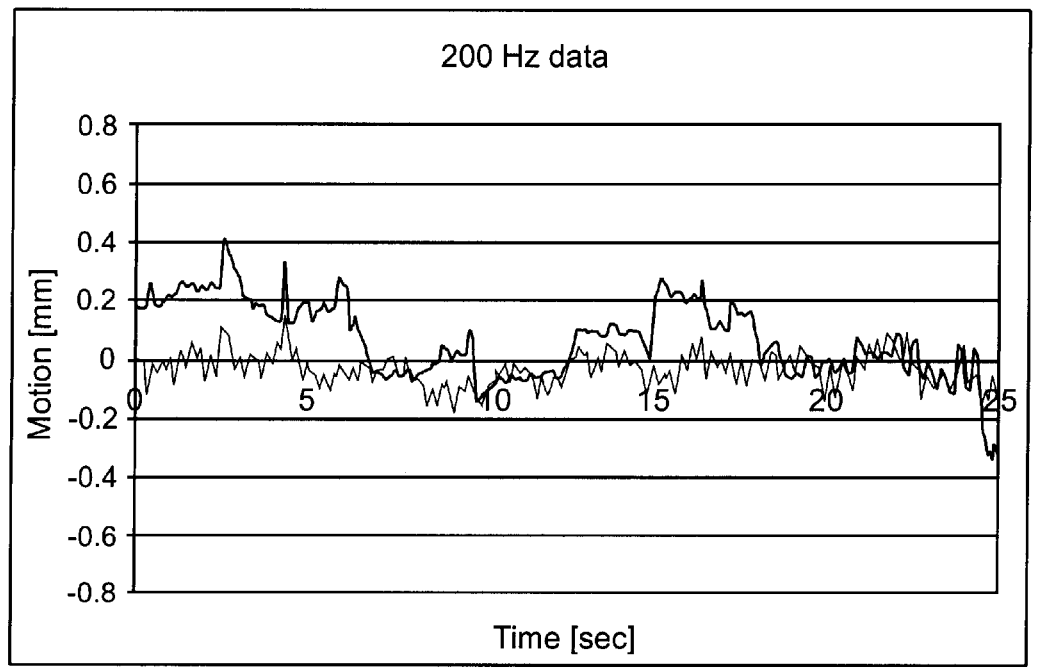
FIG. 9 graphically illustrates eye motion along the first or X and second or Y axes.

Referring now to FIG. 9, motion was recorded along the X or horizontal axis (dark line) and in the vertical orientation or Y direction (light line). FIG. 9 presents a graph of a typical patient's eye movement during a Lasik procedure as recorded by the validation tracker. This graph shows that the range of eye movements were typically smaller than +/−100 $\mu$m with occasional saccadic movements.

Figure 10:
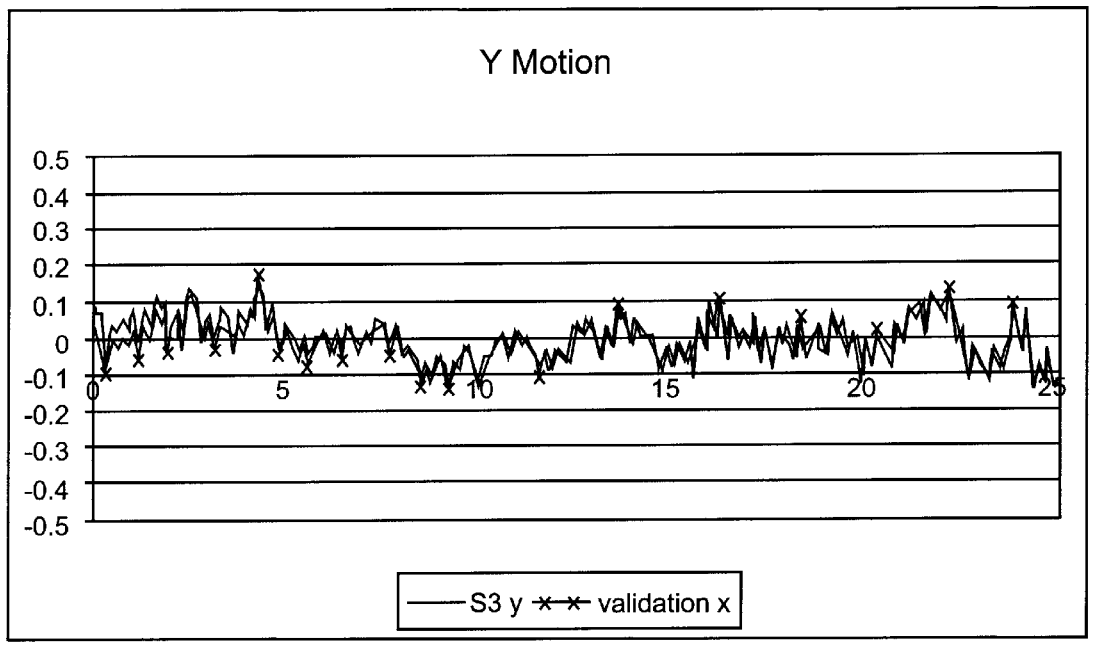
FIGS. 10 and 11 illustrate tracking performance in a first or X direction and in a second or Y direction, as described in the experimental section.
Figure 11:
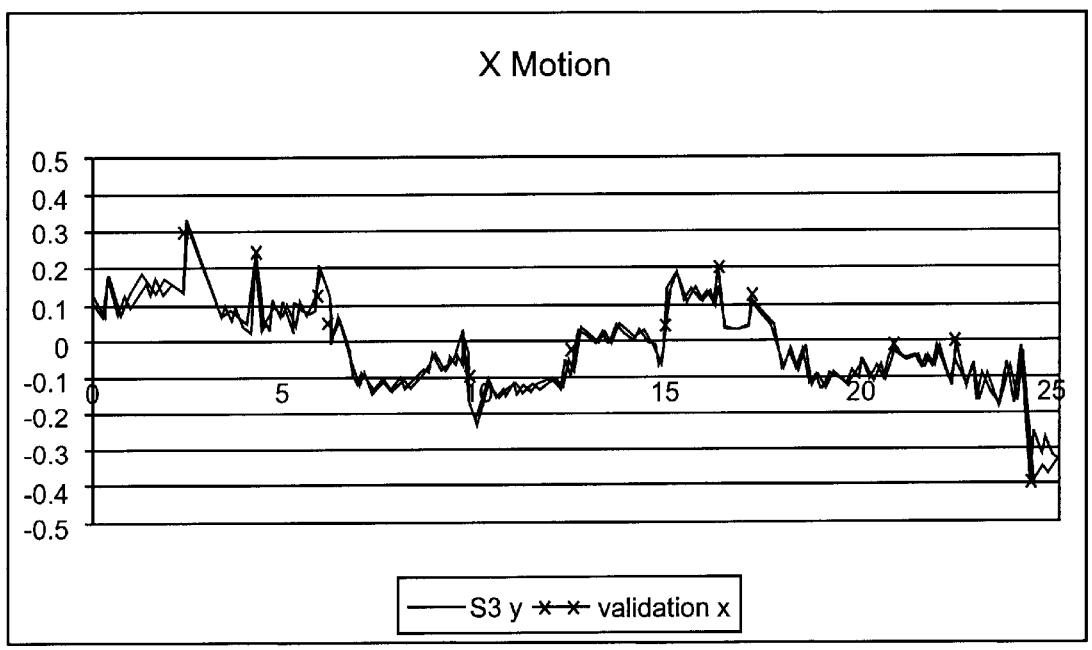

FIGS. 10–11 have relatively expanded time scales and show the latency in time between the validation tracker and the data obtained from the two-axis tracker. Comparisons of the two-axis tracker and the validation tracker are given for a total time of about 25 seconds. These graphs show that the two tracking devices correlate quite well. Small differences on the order of a few microns can be seen.

Figure 12:
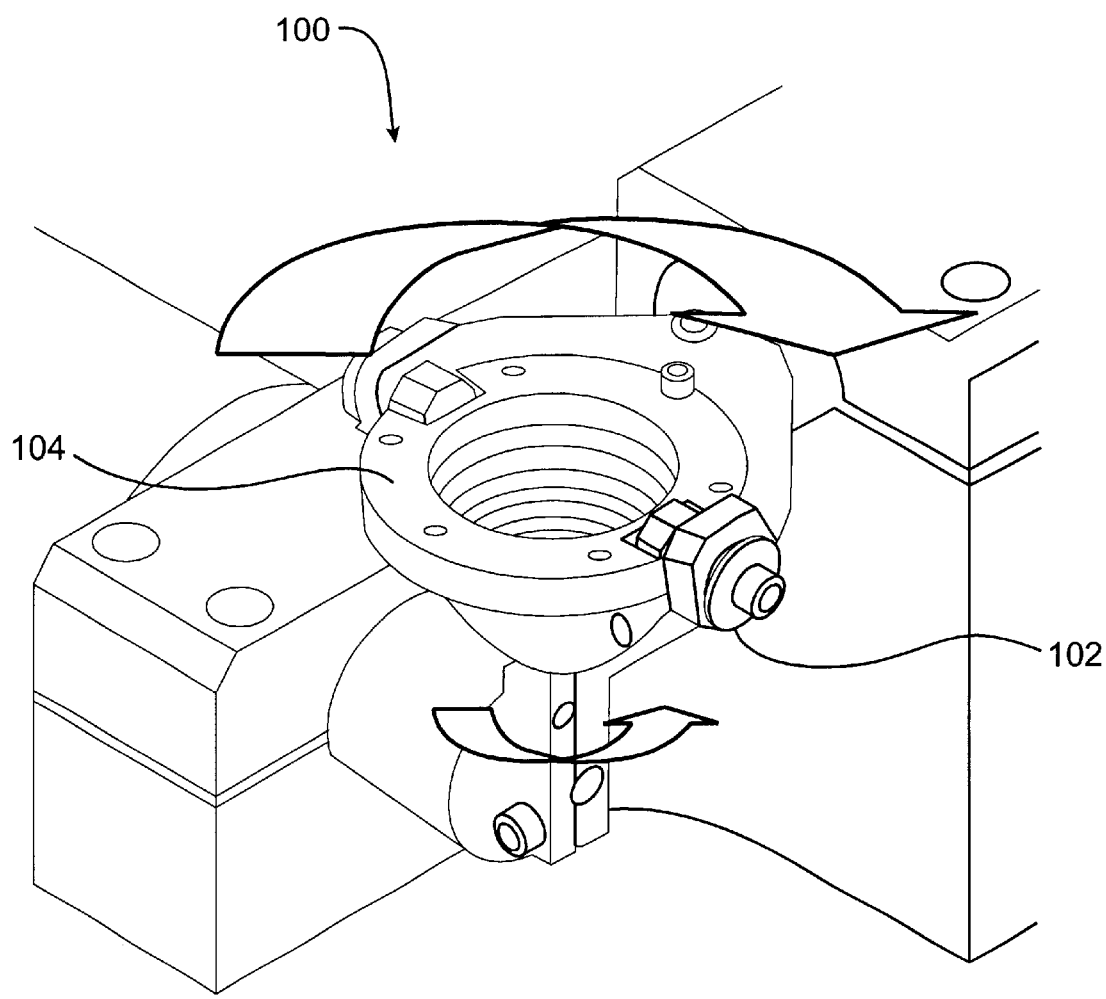
FIG. 12 is a perspective view of an eye motion simulator as described in the experimental section.

Referring now to FIG. 12, an eye motion simulator was designed and built to measure the ability of a VISX STAR S2™ with the integrated two-camera tracking system to follow movements of the eye. Simulator 100 simulates eye motion by pivoting about orthogonal axis so as to allow ablations of test plastic during movement of the test oracle. This allowed ablations to proceed during simulated rotational eye motions. Gimbals 102 were driven by a pair of computer controlled galvanometers which were calibrated to make movements of up to 0.213 $\mu$m in 5 ms. This rate corresponds to the frame-rate of the 200 Hz validation tracker.

The accuracy of a single movement of eye motion simulator 100 was designed to have a mechanical tolerance of about 25 $\mu$m, with the actual tolerance of the device being closer to about 10 $\mu$m. The fork and gimbal were manufactured from titanium and were designed to avoid excessive mass. The lever arms connecting the galvanometers to the gimbal were made of aluminum, and once assembled, the galvanometers were tuned. The galvanometers were obtained from CAMBRIDGE TECHNOLOGIES, and were controlled by a tunable controller. Tuning generally involved matching the intended mass with the actual experimental mass.

The galvanometers were tuned for supporting plastic discs having 1.5" diameter, with the material being punched from calibration plastic commercially available from VISX, INCORPORATED of Santa Clara, Calif. A ring held the plastic discs tightly on the top surface of cup 104.

The data used to drive the galvanometers was recorded during the clinical eye movement studies described above. This data was generated from equations of motions and is used to drive the galvanometers.

While eye motion simulator 100 was driven so as to move the test ablation plastic with movements equal to those of actual measured eye movements, a laser delivery system directed a standard spherical treatment onto the plastic. Once again, the STAR S2™ excimer laser system was used during this test ablation, initially without added tracking. After completion of the simulated ablation with eye movement, a new test ablation plastic was mounted on eye motion simulator 100 and this second test material was ablated while the eye motion simulator was held in a fixed position.

A third plastic ablation test sample was mounted on eye motion simulator 100, and this third test plastic was ablated while eye motion simulator 100 moved the test ablation according a recorded clinical eye motion test. For this third ablation test, the two-camera tracker provided information to the laser delivery system so as to correct the pattern of laser delivery for errors caused by eye motion. Analysis of the tracking-assisted and unassisted ablation profiles was performed by scanning the ablated plastics and measuring the differences between the ablations during motion and the intended theoretical ablation profiles. Results of a typical ablation profile are shown in FIGS. 13A and 13B.

Figure 13A:
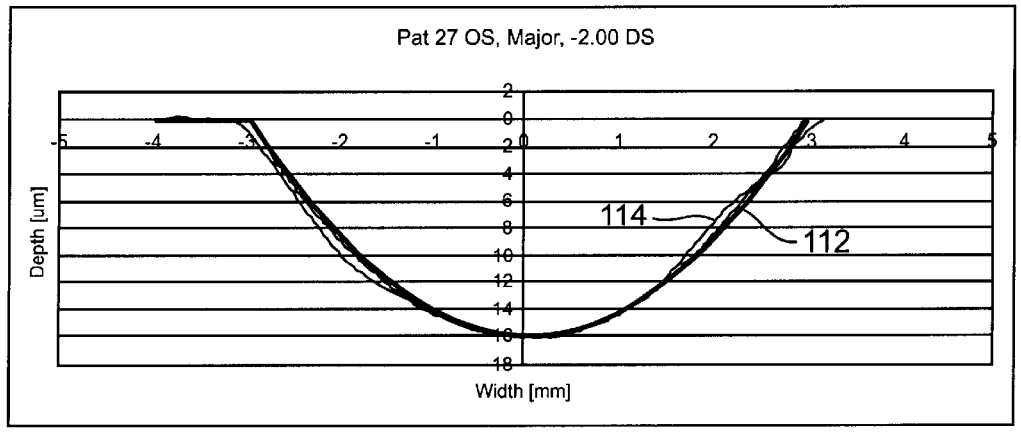
FIGS. 13A and 13B illustrate test ablation profiles and differences between an intended ablation profile and an actual ablation profile as measured using the eye motion simulator of FIG. 12.
Figure 13B:
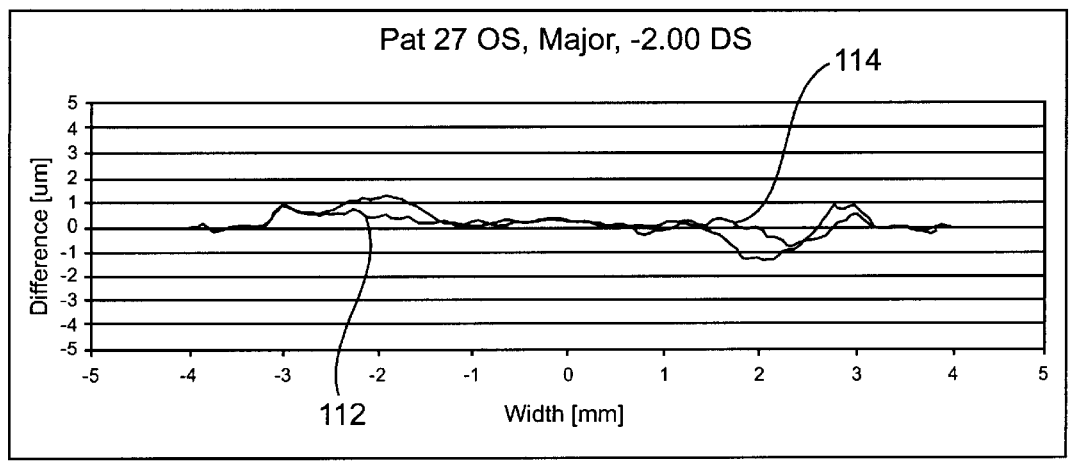

The graph of FIG. 13A shows the ablation profile along the vertical and horizontal axes for a typical ablation. The dark line shows the theoretical ablation profile. The light line 114 which is farthest from the theoretical ablation profile illustrates the profile of the test ablation performed without motion tracking. As can be seen in FIG. 13B, even without tracking the difference between the theoretical and actual ablation profiles is quite small.

The light line 112 in FIG. 13A which is closest to the theoretical ablation profile is a measured profile of a plastic ablation performed while tracking motion of the eye simulator using the two-camera tracking system. Taking the standard deviation of the difference plot illustrated in FIG. 13B over the range of −2.5 mm to 2.5 mm (a 5 mm diameter) provides a standard deviation value of 0.53 µm with tracking 112, and a 0.92 µm standard deviation without tracking 114.

Table II provides the 95% confidence test for standard deviation of difference between the measured and theoretical profiles with the tracker on and with the tracker off. As the average spherical equivalent for the clinical ablation profiles was −4.8D, the corresponding ablation depth would be about 38.4 µm. Hence, the tracking-off system error was 1.2 µm or 3.1%, while tracking-on system error was 0.6 µm or 1.5%. Thus, it is clear that the tracking system is effective.

TABLE II

|  | µ: Tracker OFF | µ: Tracker ON |
| --- | --- | --- |
| 95% CI Error | 1.2 µm | 0.60 µm |
| Percentage error | 3.1% | 1.5% |

While the exemplary embodiment has been described in some detail, by way of example and for clarity of understanding, a variety of adaptations, changes, and modifications will be obvious to those of skill in the art. Hence, the scope of the present invention is limited solely by the appended claims.

What is claimed is:

1. An apparatus for sculpting a corneal tissue of an eye so as to effect a desired change in a patient's vision, the apparatus comprising:

an energy delivery system selectively directing an energy stream along a treatment axis toward the corneal tissue;

first and second image capture devices oriented toward the eye, each image capture device having an imaging axis angularly offset from the treatment axis by between about 10 and 70 degrees; and a processor coupling the image capture devices to the energy delivery system so that the energy delivery system laterally deflects the energy stream along a first axis in response to movement of the eye sensed by the first image capture device, and so that the energy delivery system laterally deflects the energy stream along a second axis in response to movement of the eye sensed by the second image capture device.

2. The apparatus of claim 1, further comprising a laser generating the energy stream, the energy stream comprising a laser beam adapted for ablating the corneal tissue.

3. The apparatus of claim 2, wherein the energy delivery system comprises at least one offset imaging lens along an optical path of the laser beam, the imaging lens moving laterally relative to the laser beam in response to the signals from the first and second image capture devices.

4. The apparatus of claim 1, further comprising an infrared light source oriented toward the eye, wherein each image capture devices comprises a CCD sensitive to infrared light reflected by an iris and sclera of the eye, and wherein the processor comprises first and second tracker modules associated with the first and second image capture devices, respectively, the first and second tracker modules determining a position of a centroid of a pupil of the eye from the reflected infrared light.

5. An apparatus for sculpting a corneal tissue of an eye so as to effect a desired change in a patient's vision, the apparatus comprising:

an energy delivery system selectively directing an energy stream along a treatment axis toward the corneal tissue, wherein the energy stream defines a treatment axis;

first and second image capture devices oriented toward the eye, wherein the eye is disposed within first and second fields of view of the first and second image capture devices, respectively, the fields of view being angularly offset from the treatment axis; and a processor coupling the image capture devices to the energy delivery system so that the energy delivery system laterally deflects the energy stream along a first axis in response to movement of the eye sensed by the first image capture device, and so that the energy delivery system laterally deflects the energy stream along a second axis in response to movement of the eye sensed by the second image capture device.

6. The apparatus of claim 5, wherein the second field of view is offset circumferentially from the first field of view about the treatment axis.

7. The apparatus of claim 6, wherein the second field of view is offset circumferentially by about 90 degrees from the first field of view about the treatment axis.

8. The apparatus of claim 6, the eye defining an X-Y-Z coordinate system with a Z axis along an optical axis of the eye, and X-Z plane along the first axis, and a Y-Z plane along the second axis, wherein the first image capture device is disposed along the Y-Z plane and off the X-Z plane, and wherein the second image capture device is disposed along the X-Y plane and off the Y-Z plane.

9. The apparatus of claim 8, wherein the processor generates a signal indicating a distance between the energy delivery system and a feature of the eye in response to lateral positions of the feature within the first and second fields of view as sensed by the first and second image capture devices.

10. An apparatus for sensing motion of an eye, the eye having an optical axis and first and second lateral optical axes, the apparatus comprising:

a first tracker with a first image capture device and a first processor module, the first image capture device having a first imaging optical train oriented toward the eye along a first imaging axis and generating a first image, the first imaging axis angularly offset from the optical axis, the first processor module generating a first signal indicating lateral movement of the eye relative to the first imaging axis in response to the first image; and a second tracker with a second image capture device and a second processor module, the second image capture device having a second imaging optical train oriented toward the eye along a second imaging axis and generating a second image, the second imaging axis angularly offset from the optical axis and displaced circumferentially from the first imaging axis relative to the optical axis, the second processor module generating a second signal indicating lateral movement of the eye relative to the second imaging axis in response to the second image.

11. The apparatus of claim 10, further comprising a third processor module coupled to the first and second trackers, the third processor module calculating lateral displacement of the eye relative to the first and second lateral optical axes from the first and second signals.

12. The apparatus of claim 10, further comprising a laser directing a laser beam along the optical axis toward the eye so as to ablate corneal tissue of the eye to effect a predetermined change in an optical characteristic of the eye.

13. A method for sensing movement of an eye having an optical axis and first and second lateral axes, the method comprising:

sensing movement of the eye along the first lateral axis with a first imaging capture device, the first image capture device disposed along a first imaging path offset from the optical axis by an angle in the range from about 10 degrees to about 70 degrees; and sensing movement of the eye along the second lateral axis with a second imaging capture device disposed along a second imaging path offset from the optical axis by an angle in the range from about 10 degrees to about 70 degrees, the second imaging path displaced circumferentially about the optical axis relative to the first imaging path.

14. The method of claim 13, further comprising directing a pattern of laser energy toward the eye so as to effect a desired change in an optical characteristic of the eye, and laterally displacing the laser energy in response to the sensed movement of the eye from the first and second image capture devices to enhance alignment between the pattern and the eye when the eye moves.

15. The method of claim 14, wherein the laser energy is laterally displaced in response to sensed voluntary movements of the eye or head, and wherein rapid saccadic movements of the eye are not tracked.

16. The method of claim 13, further comprising determining positional information of the eye along the optical axis using signals from at least one of the image capture devices.

* * * * *